(12) United States Patent
Crampton

(10) Patent No.: US 8,703,983 B2
(45) Date of Patent: Apr. 22, 2014

(54) PROCESS FOR PRODUCING PROPYLENE OXIDE USING A PRETREATED EPOXIDATION CATALYST

(75) Inventor: Hannah L. Crampton, Lake Jackson, TX (US)

(73) Assignee: Dow Global Technologies, LLC, Midland, MI (US)

( * ) Notice: Subject to any disclaimer, the term of this patent is extended or adjusted under 35 U.S.C. 154(b) by 0 days.

(21) Appl. No.: 13/637,072

(22) PCT Filed: Mar. 22, 2011

(86) PCT No.: PCT/US2011/000523
§ 371 (c)(1),
(2), (4) Date: Sep. 25, 2012

(87) PCT Pub. No.: WO2011/119217
PCT Pub. Date: Sep. 29, 2011

(65) Prior Publication Data
US 2013/0018196 A1     Jan. 17, 2013

Related U.S. Application Data

(60) Provisional application No. 61/317,390, filed on Mar. 25, 2010.

(51) Int. Cl.
*C07D 303/00* (2006.01)

(52) U.S. Cl.
USPC .......................................... 549/512; 549/513

(58) Field of Classification Search
USPC ................................. 549/512, 513
See application file for complete search history.

(56) References Cited

U.S. PATENT DOCUMENTS

| | | |
|---|---|---|
| 4,410,501 A | 10/1983 | Taramasso et al. |
| 6,479,680 B1 | 11/2002 | Bassler et al. |
| 6,849,162 B2 | 2/2005 | Teles et al. |
| 6,867,312 B1 | 3/2005 | Jubin, Jr. et al. |
| 6,881,853 B2 | 4/2005 | Teles et al. |
| 6,884,898 B1 | 4/2005 | Miller |
| 6,960,671 B2 | 11/2005 | Cooker et al. |
| 7,173,143 B2 | 2/2007 | Bender et al. |
| 7,332,634 B2 | 2/2008 | Bassler et al. |
| 7,378,536 B2 | 5/2008 | Goebbel et al. |
| 7,449,590 B2 | 11/2008 | Tsuji et al. |

FOREIGN PATENT DOCUMENTS

WO      2007013739      2/2007

OTHER PUBLICATIONS

International Search Report and Written Opinion from related PCT application PCT/US2011/000523 dated Jun. 14, 2011, 13 pages.
International Preliminary Report on Patentability from related PCT application PCT/US2011/000523 dated May 22, 2012, 13 pages.
Nur, et al. "Phase-Boundary Catalysis of Alkene Epoxidation with Aqueous Hydrogen Peroxide Using Amphiphilic Zeolite Particles Loaded with Titanium Oxide", Journal of Catalysis, Academic Press, vol. 204, No. 2, Dec. 10, 2001, XP004432346, 402-408.
Zhang, et al. "Effects of Organic Solvent Addition on the Epoxidation of Propene Catalyzed by TS-1", Reaction Kinetics and Catalysis Letters, Springer Science+Business Media, Dordrecht, NL, vol. 92, No. 1, Sep. 21, 2007, pp. 49-54.
Clerici, et al. "Epoxidation of Lower Olefins with Hydrogen Peroxide and Titanium Silicalite", Journal of Catalysis, 1993, 140, 71-83.

*Primary Examiner* — Nizal Chandrakumar
(74) *Attorney, Agent, or Firm* — Brooks, Cameron & Huebsch, PLLC

(57) ABSTRACT

A process for preparing propylene oxide by epoxidizing propylene with an oxidant in the presence of a pretreated catalyst; wherein the catalyst comprises an activated titanium silicalite with MFI structure (TS-1) catalyst; and wherein the catalyst has been activated by pretreatment with methanol to form the pretreated catalyst. The pretreated TS-1 catalyst may be used in the epoxidizing propylene reaction with no additional methanol added; and the pretreated catalyst has equivalent activity to TS-1 catalyst used with large excesses of methanol.

8 Claims, No Drawings

PROCESS FOR PRODUCING PROPYLENE OXIDE USING A PRETREATED EPOXIDATION CATALYST

This application is a National Stage application under 35 U.S.C. 371 of PCT/US2011/000523, filed on Mar. 22, 2011 and published as WO 2011/119217 A1 on Sep. 29, 2011, which claims the benefit of U.S. Provisional Application Ser. No. 61/317,390 filed Mar. 25, 2010, the entire contents of which are incorporated herein by reference in its entirety.

BACKGROUND OF THE INVENTION

1. Field of the Invention

The present invention relates to a process for preparing propylene oxide by reacting propylene and a peroxide compound, in the presence of a pretreated titanium silicalite epoxidation catalyst.

2. Description of Background and Related Art

In the preparation of propylene oxide, the customary processes in the prior art involve reacting propylene with hydrogen peroxide to produce propylene oxide. The process is usually carried out in one or more stages. For example, U.S. Pat. Nos. 6,479,680; 6,849,162; 6,867,312; 6,881,853; 6,884,898; 6,960,671; 7,173,143; 7,332,634; 7,378,536; and 7,449,590; all of which are incorporated herein by reference, disclose a process for the preparation of propylene oxide using hydrogen peroxide in the presence of a catalyst such as a titanium silicalite catalyst, and in the presence of a solvent such as methanol.

A problem with the prior art propylene oxide production processes relates to the use of methanol as a solvent for the processes. While methanol is a necessary reaction component of the peroxide reaction to obtain high activity, the methanol is generally used in large excesses (for example, from 50-90 weight percent) to ensure that the reaction mixture remains as one liquid phase. For example, Clerici et al., "Epoxidation of Lower Olefins with Hydrogen Peroxide and Titanium Silicalite," Journal of Catalysis, 1993, 140, 71-83, discloses a process that is representative of titanium silicalite/hydrogen peroxide epoxidation processes, wherein the methanol level used in one example is approximately 97%. The use of an excessive amount of methanol, as described in the prior art processes, results in the formation of a single phase during the reaction; and the prior art processes suffer from the formation of byproducts, for example, byproducts formed from the reaction of methanol and water, wherein such byproducts are solubilized in the organic phase by methanol, with propylene oxide. The use of large quantities of methanol also results in the need for large towers for propylene oxide production facilities, and for a high energy consumption for the purification of the product produced on a commercial scale.

The problems of the prior art processes may be solved by reducing the methanol concentration or removing methanol entirely from the reaction mixture. However, in the epoxidation of propylene, reducing or eliminating methanol concentration in the known processes creates a reaction system with two liquid phases, which results in lower propylene oxide yield, lower hydrogen peroxide ($H_2O_2$) selectivity to propylene oxide, and/or longer reaction times.

Zhang et al., "Effects of Organic Solvent Addition on the Epoxidation of Propene Catalyzed by TS-1," Reaction Kinetics and Catalysis Letters, 2007, 92(1), 49-54, discusses the use of solvent mixtures with methanol for the epoxidation of propylene. Zhang et al. disclose that replacing approximately 24% of the methanol in Zhang et al.'s system with other solvents such as $CCl_4$, toluene, or 1,2-dichloroethane, results in increased selectivity and less clogging of the catalyst pores, as measured by thermogravimetric analysis (TGA) and pore volume analyses. The mixture of methanol and 1,2-dichloroethane, of Zhang et al.'s system, which gives a total methanol composition of 60%, inhibits the decomposition of $H_2O_2$; and inhibits the reaction of propylene oxide to form propylene glycol and propylene glycol mono-methyl ethers, while retaining the $H_2O_2$ conversion as compared to the use of methanol only. However, although Zhang et al. describe using mixtures of solvents to increase the selectivity of the reaction, the total solvent amounts used create single phase reaction conditions. Thus, prior art processes which use solvent mixtures still use a high level of methanol and/or a single liquid phase.

In summary, the disadvantages of the known processes described in the above prior art include the following:

(1) The prior art processes use high levels of methanol; and thus, the high levels of methanol must be separated from the product and recycled. This creates high energy usage for the process and associated high costs.

(2) The prior art processes use a first separation step wherein solvent and unreacted reactant are recovered and recycled. This requires the use of a high temperature in the bottoms of distillations towers, which in turn requires the use of high temperatures throughout the distillation towers. Any water in the feed to the distillation towers remains in contact with the product in the distillation towers; and thus the available water provides an opportunity to react with the product to form undesired by-products.

It is therefore desired to provide a process that does not have the problems of the above prior art processes and that can be operated at reaction conditions which address all of the above issues and maintain a high catalyst activity

SUMMARY OF THE INVENTION

The present invention provides a propylene oxide production process which uses substantially no methanol as a solvent as compared to previously known processes.

The present invention is directed to a process for preparing propylene oxide by epoxidizing propylene with an oxidant in the presence of a pretreated catalyst; wherein the catalyst comprises an activated titanium silicalite with MFI structure (TS-1) catalyst; and wherein the catalyst has been activated by pretreatment with methanol to form the pretreated catalyst. The pretreated TS-1 catalyst may be used in the epoxidation of propylene reaction with no additional methanol added as a solvent to the reaction mixture during the reaction of epoxidizing the propylene; and the pretreated catalyst of the present invention has equivalent activity compared to a non-pretreated TS-1 catalyst used in combination with large excesses of methanol as a solvent in accordance with the processes known in the prior art.

In one embodiment, the present invention includes a modified TS-1 catalyst comprising a TS-1 catalyst which has been treated with methanol, and optionally, air dried prior to the use of such modified catalyst. The catalyst is modified, i.e., treated with methanol, before the catalyst is used in the reaction of epoxidizing propylene to form propylene oxide. By pretreating the TS-1 catalyst with methanol, resulting pretreated TS-1 catalyst becomes activated and ready for use in a propylene epoxidation reaction process. No additional solvent is necessary in the propylene reaction composition, which promotes the formation of two liquid phases.

The present invention is advantaged compared to those of the prior art which use 50 weight percent (wt %) or more methanol because the separation and isolation of the epoxide from the reaction mixture is facilitated. The removal of methanol as a solvent results in the formation of two liquid phases, which can be decanted after the reaction to obtain an epoxide-rich organic phase. The present invention is advantaged compared to the prior art processes because by pretreating the catalyst with methanol and then using the modified catalyst in the process of the present invention, a higher selectivity of $H_2O_2$ to propylene oxide, a higher propylene oxide yield, and a higher selectivity of propylene oxide versus byproducts can be achieved.

The advantages of the system of the present invention include decreased losses of propylene oxide by solvolysis and decreased energy costs for separation, while maintaining fast reaction times. The present invention also presents an advantage over reactor compositions which use amounts of methanol of 50 wt % or higher as a solvent by decreasing by at least 80% the formation of byproduct in the reaction.

Another advantage of the present invention is lower equipment cost and lower energy usage due to not having to separate out, recover and/or recycle methanol when used as a solvent in a reaction mixture.

DETAILED DESCRIPTION OF THE INVENTION

One broad embodiment of the present invention comprises a process for preparing propylene oxide comprising epoxidizing propylene with an oxidant in the presence of a pretreated catalyst; wherein the pretreated catalyst comprises an activated titanium silicalite with MFI structure (TS-1) catalyst; and wherein the catalyst has been activated by pretreatment with methanol in an effective amount to sufficiently activate the catalyst and form the pretreated catalyst.

The process for preparing an activated catalyst for use in the present invention comprises pretreating a TS-1 catalyst with methanol. The pretreating step includes for example, the step of contacting a TS-1 catalyst with the methanol under conditions to have the methanol bond to the TS-1 catalyst prior to use of the catalyst.

The catalyst useful in the process of the present invention includes known titanium silicalite catalysts. The TS-1 catalysts used in the present invention process may be selected from commercially available catalyst such as TS-1 from Süd Chemie, Polimeri Europa, or Clean Science, for example. Alternatively, the TS-1 catalysts can be manufactured by any of the known processes such as those described in U.S. Pat. No. 4,410,501, for example.

In other embodiments of the present invention, other titanium silicates may be used such as titanium-silicalites with a MEL or intermediate MFI/MEL structure and titanium-silicalites from beta zeolites containing titanium and having a BEA structure. Other titanium containing zeolite catalysts generally known as TS-2, TS-3, Ti-MCM-22, Ti-MWW, ZSM-48 and ZMS-12 can also be used for preparing the catalyst of the present invention process.

The concentration of the TS-1 catalyst used in the present invention is generally from about 0.1 weight percent (wt %) to about 50 wt %, preferably from about 0.1 wt % to about 25 wt % and more preferably from about 1 wt % to about 10 wt %.

The methanol useful in the present invention includes known methanol compounds commercially available such as methanol from Fisher Scientific.

The amount of methanol (MeOH) used to pretreat the TS-1 catalyst is generally at a mole ratio of MeOH to TS-1 catalyst of from about 0.1:1 MeOH:TS-1 to about 100:1 MeOH:TS-1, preferably, from about 1:1 MeOH:TS-1 to about 100:1 MeOH:TS-1, more preferably from about 1:1 MeOH:TS-1 to about 50:1 MeOH:TS-1, and most preferably from about 5:1 MeOH:TS-1 to about 10:1 MeOH:TS-1.

The fraction (the at least a portion) of titanium that is chemically bonded with methanol in TS-1 catalyst generally is from about 50% to about 200%, preferably from about 100% to about 200% and more preferably from about 150% to about 200%; as determined by infrared (IR) spectroscopy and TGA; and based on the theory that each Ti molecule can bind two MeOH molecules.

Generally, the process of pretreating the catalyst includes for example contacting a TS-1 catalyst with the methanol at a temperature of from about −20° C. to about 60° C., preferably from about 0° C. to about 60° C., and more preferably from about 25° C. to about 60° C. The contacting step may be carried out by known methods and equipment such as mechanical stirring, flowing through a packed catalyst bed, or soaking in a container; and the like.

The contacting step can be carried out for a pre-determined period of time sufficient to bond the methanol to the TS-1 catalyst, such as for example, generally for about 1 minute to about 24 hours, preferably from about 5 minutes to about 1 hour, and more preferably from about 30 minutes to about 1 hour.

After the contacting step the pretreated catalyst may be separated from the excess methanol. Any separation method known in the art may be used such as filtering, centrifuging, evaporating, decantation, and the like.

Optionally, the isolated pretreated catalyst may be dried before or after filtering the catalyst. Any drying method known in the art may be used such as by flowing air, placement in a dessicator, or placement in an oven at temperatures below 65° C. with or without the presence of air.

After isolating the pretreated catalyst, the pretreated catalyst may be used in the process of epoxidizing propylene to form propylene oxide.

As aforementioned, the pretreated catalyst product of the present invention preferably contains at least a portion of methanol chemically bonded to titanium atoms of the catalyst. The fraction of titanium that is chemically bonded with methanol in TS-1 catalyst generally is from about 50% to about 200%, preferably from about 100% to about 200% and more preferably from about 150% to about 200%; as determined by IR spectroscopy at a frequency of 950-970cm$^{-1}$, depending on the TS-1 catalyst crystal size; and based on the theory that each Ti molecule can bind two methanol molecules.

The chemisorption of MeOH onto Ti causes a shift in the frequency of the Ti-O stretch to higher wavenumbers. The chemisorption is also evidenced by evolution of material in a TGA at approximately 400° C. Optionally, methanol that is not chemically bonded but is retained in the pores of the catalyst may be present as well. This is not seen in the IR spectrum at the indicated range, and evolves at approximately 65° C. in the TGA.

The pretreated catalyst described above may be used in a process of the present invention for oxidizing propylene by reacting the propylene with an oxidant, such as hydrogen peroxide, under reaction conditions to prepare propylene oxide; wherein this oxidizing reaction (also referred to herein as an epoxidation reaction) is catalyzed by the methanol pretreated TS-1 catalyst which has been activated by pretreatment with methanol as described above.

The propylene useful in the epoxidation process of the present invention includes any propylene compound known in the art such as propylene commercially available from Sigma Aldrich. Alternatively, the propylene can be manufactured by known processes.

The concentration of the propylene used in the epoxidation process is generally from about 10 wt % to about 90 wt %, preferably from about 20 wt % to about 80 wt %, and more preferably from about 30 wt % to about 70 wt %.

The oxidant useful in the propylene epoxidation process of the present invention includes known oxidant compounds such as peroxocompounds such as a hydroperoxide including for example hydrogen peroxide, commercially available from Fisher Scientific. Examples of other hydroperoxides that may be used include, but are not limited to, tert-butyl hydroperoxide, ethylbenzene hydroperoxide, acetyl peroxide, benzoyl peroxide, methyl ethyl ketone peroxide, cumene peroxide, and combinations thereof.

In one embodiment of the present invention, the epoxidation of propylene may be carried out preferably using hydrogen peroxide. An advantage of this process is the avoidance of forming by-products and/or co-products.

The concentration of the oxidant used in the epoxidation process is generally from about 1 wt % to about 30 wt %, preferably from about 1 wt % to about 15 wt %, and more preferably from about 1 wt % to about 7 wt %.

Generally, the propylene epoxidation process includes for example mixing the propylene with an oxidant at a temperature of from about 0° C. to about 60° C., preferably from about 10° C. to about 50° C., and more preferably from about 25° C. to about 45° C. The mixing step may be carried out by known methods and equipment such as a stirred batch reactor, a plug flow reactor, a continuously stirred tank reactor, a fluidized bed reactor, a loop reactor, or a tubular reactor, and the like.

After the mixing step the resultant propylene oxide may be recovered from the reaction mixture. Any recovery method known in the art may be used such as decantation, extraction, evaporation, or distillation, and the like.

After isolating the propylene oxide, the propylene oxide may be further used as an intermediate product in various processes such as for making coatings and composites.

In the process of producing propylene oxide from propylene, the process steps may include the following steps: addition of reactants, mixing the reactants in the presence of a catalyst, separation of the reactants from the catalyst, separation of propylene from the reaction mixture, and optionally, recycle of unreacted propylene and/or solvents.

Some of the advantages of the process of the present invention includes for example, (1) no methanol is needed or used to prepare propylene oxide product; the use of no methanol facilitates separation and isolation of the desired propylene oxide product; (2) an increase in yield of propylene oxide product; the propylene oxide yield is preserved, while the losses of propylene oxide to byproducts is reduced; (3) a decrease in methanol byproducts production, thus providing a purer propylene oxide product; and (4) lower equipment cost and lower energy usage due to not having to separate out, recover and/or recycle methanol when used as a solvent in a reaction mixture.

EXAMPLES

The following examples and comparative examples further illustrate the present invention in detail but are not to be construed to limit the scope thereof. Unless otherwise indicated, all parts and percentages are by weight. Unless otherwise specified, all instruments and chemicals used are commercially available.

In the following Examples, various terms and designations are used such as for example, "GC" stands for gas chromatography; "PO" stands for propylene oxide; "biphasic" means two liquid phases which are present in addition to any solid or gas phases which may be present in a reaction mixture.

In the following Examples, standard analytical equipment and methods are used including the following:

Gas chromatography (GC) is performed on an HP 6890 series G1530A GC with a HP 7682 series injector and flame ionization detector.

The amount of hydrogen peroxide is analyzed by iodometric titration using 0.01 normality (N) sodium thiosulfate. The hydrogen peroxide concentration is calculated as follows: parts per million (ppm) hydrogen peroxide=(milliliter (ml) titrant used) (0.01 N) (17000)/g sample. Titrations are performed using a Mettler Toledo DL5x V2.3 titrator with a DM140 sensor.

Example 1

Part A.—Pretreatment of the TS-1 Catalyst

TS-1 catalyst (6.90 g) is stirred with MeOH (50 mL) at 25° C. for 1 hour. The catalyst is vacuum filtered through a 0.45 µm filter paper and air-dried in a dessicator. The resulting TS-1 catalyst prepared this way will hereafter be referred to as the "pretreated TS-1 catalyst".

Part B.—Propylene Oxide Process using the Pretreated TS-1 Catalyst

Propylene (363.10 g, obtainable from Sigma Aldrich) and pretreated TS-1 catalyst (7.173 g, Si/Ti=~30) prepared in Part A. above are added to a 750-mL jacketed glass reactor with a stainless steel cooling coil, thermocouple, mechanical stirrer, addition funnel, $N_2$ purge with gas scrubber, and reflux condenser/cold finger combination. 32 wt %/aqueous (aq.) hydrogen peroxide (80.02 g) is charged to the addition funnel, and then is added to the reactor slowly after the propylene/catalyst mixture is brought to 25.5° C. The mixture is stirred at 600 rpm, and the reaction is maintained at approximately 25° C. using the cooling coil.

After 300 minutes, the reactor contents are drained equally into two 250 mL centrifuge tubes, and then centrifuged at 3000 rpm and 0° C. for 30 minutes. The liquid is decanted from the catalyst into a separatory funnel, where resultant organic and aqueous phases are collected separately.

The organic and the aqueous phases are analyzed by GC and the amount of peroxide remaining is determined by titration with sodium thiosulfate.

While the present disclosure includes a limited number of embodiments, the scope of the present invention should be limited only by the attached claims and not by the embodiments herein as other embodiments are possible to those skilled in the art having benefit of this disclosure.

What is claimed is:

1. A process for preparing propylene oxide comprising epoxidizing propylene with an oxidant in the presence of a pretreated titanium-containing zeolite catalyst with MFI structure where no methanol is added as a solvent to the process; wherein the pretreated catalyst comprises an activated titanium silicalite with MFI structure (TS-1) catalyst comprising a pretreated titanium-containing zeolite catalyst being pretreated with methanol at a mole ratio of methanol to TS-1 catalyst from 0.1:1 methanol:TS-1 catalyst to 100:1 methanol:TS-1 catalyst at a temperature of from about −20° C. to about 60° C. for about 1 minute to about 24 hours and air dried at a temperature of below 65° C. prior to employing the TS-1 catalyst in the propylene epoxidation reaction.

2. The process of claim 1, wherein at least a portion of the methanol is chemically bound to the TS-1 catalyst; and wherein the fraction of titanium that is chemically bonded with methanol in titanium silicalite-1 comprises from about 50% to about 200%.

3. The process of claim 1, wherein said pretreated catalyst is in the form of a solid activated catalyst separate from excess methanol and wherein said pretreated catalyst maintains its reactivity in an oxidation reaction.

4. The process of claim 1, wherein the oxidant comprises a peroxide compound.

5. The process of claim 1, wherein the oxidant comprises hydrogen peroxide.

6. The process of claim 1, wherein the pretreating with methanol is carried out at a temperature of from about 0° C. to about 60° C.

7. The process of claim 1, including the step of separating the excess methanol from the pretreated catalyst.

8. The process of claim 7, wherein the separating step comprises filtering, centrifuging or evaporating.

* * * * *

UNITED STATES PATENT AND TRADEMARK OFFICE
CERTIFICATE OF CORRECTION

PATENT NO. : 8,703,983 B2
APPLICATION NO. : 13/637072
DATED : April 22, 2014
INVENTOR(S) : Hannah L. Crampton It is certified that error appears in the above-identified patent and that said Letters Patent is hereby corrected as shown below:

Title page, item [73] Assignee "Dow Global Technologies, LLC" should read "Dow Global Technologies LLC"

Signed and Sealed this
Fifth Day of May, 2015

Michelle K. Lee
*Director of the United States Patent and Trademark Office*